US008408073B2

(12) United States Patent
Sparks et al.

(10) Patent No.: US 8,408,073 B2
(45) Date of Patent: Apr. 2, 2013

(54) MICROFLUIDIC DEVICE AND METHOD OF USE

(75) Inventors: Douglas Ray Sparks, Whitmore Lake, MI (US); Richard Thayre Smith, Saline, MI (US); Nader Najafi, Ann Arbor, MI (US)

(73) Assignee: Integrated Sensing Systems Inc., Ypsilanti, MI (US)

( * ) Notice: Subject to any disclaimer, the term of this patent is extended or adjusted under 35 U.S.C. 154(b) by 15 days.

(21) Appl. No.: 13/270,817

(22) Filed: Oct. 11, 2011

(65) Prior Publication Data

US 2012/0260718 A1 Oct. 18, 2012

Related U.S. Application Data

(60) Division of application No. 12/267,263, filed on Nov. 7, 2008, now abandoned, and a continuation-in-part of application No. 11/306,395, filed on Dec. 27, 2005, now abandoned.

(60) Provisional application No. 61/003,089, filed on Nov. 15, 2007, provisional application No. 61/002,256, filed on Nov. 8, 2007, provisional application No. 60/721,220, filed on Sep. 29, 2005, provisional application No. 60/639,406, filed on Dec. 27, 2004.

(51) Int. Cl.
*G01F 1/84* (2006.01)

(52) U.S. Cl. .............................. 73/861.356; 73/861.355
(58) Field of Classification Search ............. 73/861.355, 73/861.356
See application file for complete search history.

(56) References Cited

U.S. PATENT DOCUMENTS 6,471,487 B2 * 10/2002 Keilty et al. ............. 73/861.355
6,477,901 B1 * 11/2002 Tadigadapa et al. ...... 73/861.352

* cited by examiner

*Primary Examiner* — Lisa Caputo
*Assistant Examiner* — Punam Roy
(74) *Attorney, Agent, or Firm* — Hartman Global IP Law; Gary M. Hartman; Domenica N. S. Hartman

(57) ABSTRACT

A microfluidic device and sensing method that utilize a resonating tube configured to have sufficient sensitivity to be capable of sensing the volume of a gas present as bubbles in a liquid or the flow rate and/or density of a gas or gas mixture flowing through the tube. The tube has a freestanding tube portion supported above a surface of a substrate so as to be capable of vibrating in a plane normal to the surface of the substrate. As a gas-containing fluid flows through an internal passage of the tube, a drive signal vibrates the freestanding tube portion at a resonant frequency thereof. Coriolis-induced deflections of the freestanding tube portion are sensed relative to the substrate to produce an output corresponding to the sensed deflections, and the drive signal and/or the output are assessed to determine the volume, density and/or flow rate of the gas of the gas-containing fluid.

20 Claims, 9 Drawing Sheets

MICROFLUIDIC DEVICE AND METHOD OF USE

CROSS REFERENCE TO RELATED APPLICATIONS

This is a division patent application of co-pending U.S. patent application Ser. No. 12/267,263, filed Nov. 7, 2008, which claims the benefit of U.S. Provisional Application No. 61/002,256 filed Nov. 8, 2007, and U.S. Provisional Application No. 61/003,089 filed Nov. 15, 2007, the contents of which are incorporated herein by reference. Co-pending U.S. patent application Ser. No. 12/267,263 is also a continuation-in-part patent application of co-pending U.S. patent application Ser. No. 11/306,395, filed Dec. 27, 2005, which claims the benefit of U.S. Provisional Application No. 60/639,406, filed Dec. 27, 2004, and U.S. Provisional Application No. 60/721,220, filed Sep. 29, 2005. The contents of these prior applications are also incorporated herein by reference.

BACKGROUND OF THE INVENTION

The present invention generally relates to devices and methods for measuring properties of fluids. More particularly, this invention relates to a microfluidic device having a resonating tube capable of sensing the volume of a gas present as bubbles in a liquid flowing through the tube, or the flow rate and/or density of a gas or gas mixture flowing through the tube.

Fluid delivery devices capable of precise measurements find use in a variety of industries, including medical treatment systems such as drug infusion and anesthesia, energy and fuel systems such as fuel cells, and consumer goods. Various types of flow rate and concentration sensors have been proposed, including electrolytic, refractometer, ultrasonic, electrochemical, electromagnetic, and electromechanical sensors. An example of the latter is a Coriolis-based microfluidic device disclosed in commonly-assigned U.S. Pat. No. 6,477,901 to Tadigadapa et al., whose contents relating to the fabrication and operation of a Coriolis-based sensor are incorporated herein by reference.

A microfluidic device 10 of a type disclosed by Tadigadapa et al. is represented in FIGS. 1 and 2. The device 10 is shown as including a micromachined tube 14 extending from a base 28 on a substrate 12, with a freestanding portion 16 of the tube 14 suspended above a surface 18 of the substrate 12. Drive and sensing electrodes 22 and 24 are located on the substrate surface 18 beneath the freestanding portion 16 of the tube 14, and bond pads 32 (only one of which is shown) are provided for transmitting input and output signals to and from the device 10. The drive electrode 22 can be, for example, capacitively coupled to the tube 14 for capacitively (electrostatically) driving the freestanding portion 16 at or near resonance, while the sensing electrodes 24 sense (e.g., capacitively, optically, etc.) the deflection of the resonating tube 14 relative to the substrate 12 and provide feedback to enable the vibration frequency induced by the drive electrode 22 to be controlled with appropriate circuitry.

With a fluid entering the device 10 through an inlet port 26 and flowing through an internal passage 20 within the tube 14, the freestanding portion 16 can be vibrated at or near resonance by the drive electrode 22 to ascertain certain properties of the fluid, such as flow rate and density, using Coriolis force principles. In particular, as the freestanding portion 16 is driven at or near resonance by the drive electrode 22, the sensing electrodes 24 sense a twisting motion of the freestanding portion 16, referred to as the Coriolis effect, about the axis of symmetry of the freestanding portion 16 (i.e., parallel to the legs of the freestanding portion 16). Because the twisting motion is more readily detectable along the parallel legs of the freestanding portion 16, the sensing electrodes 24 may be positioned along the entire lengths of the legs. The degree to which the freestanding portion 16 twists (deflects) during a vibration cycle as a result of the Coriolis effect can be correlated to the mass flow rate of the fluid flowing through the tube 14, while the density of the fluid is proportional to the frequency of vibration at resonance.

Notable advantages of the Coriolis microfluidic device 10 include the miniaturized scale to which it can be fabricated and its ability to precisely analyze very small quantities of fluids. In FIG. 2, the device 10 is schematically shown as enclosed by a capping wafer 30 to allow for vacuum packaging that further improves the performance of the device 10 by reducing air damping effects. In addition, FIG. 2 shows a getter material 34 placed in the enclosure to assist in reducing and maintaining a low cavity pressure.

The microfluidic device 10 represented in FIGS. 1 and 2 and disclosed in Tadigadapa et al. can be used in a wide variety of applications, as evident from commonly-assigned U.S. Pat. Nos. 6,637,257, 6,647,778, 6,932,114, 7,059,176, 7,228,735, 7,263,882, 7,354,429 and 7,437,912, U.S. Published Patent Application Nos. 2004/0171983, 2005/0126304, 2005/0284815, 2005/0235759, 2006/0211981, 2007/0151335, 2007/0157739, 2008/0154535, and pending U.S. patent application Ser. Nos. 12/031,839, 12/031,860, 12/106,642 and 12/143, 942. As particular examples, U.S. Pat. No. 7,263,882 teaches that chemical concentrations, including those of fuel cell solutions, can be measured by sensing changes in fluid density as a fluid sample flows through a microchannel within a resonating tube of a Coriolis-based microfluidic device, and U.S. Published Patent Application No. 2007/0157739 teaches the capability of detecting potential measurement errors attributable to second phases such as gas bubbles in a fluid being evaluated by a resonating tube of a Coriolis-based microfluidic device. A particular example disclosed in 2007/0157739 is a fuel cell power generation process, during which carbon dioxide, air, and other gases generated or dissolved in a fuel cell solution may form bubbles that can cause errors in chemical concentration outputs based on density. As solution, 2007/0157739 teaches modifications to the construction and operation of the Coriolis-based fluid sensing device of Tadigadapa et al. to promote the detection of second phases such as gas bubbles in a fuel cell solution.

While capable of detecting the presence of gas bubbles in a liquid, Coriolis microfluidic devices of the type taught by Tadigadapa et al. have limited capability for measuring the volume of gas bubbles present in a liquid or the flow rate or density of a gas or gas mixture. In particular, while U.S. Pat. No. 7,263,882 and U.S. Published Patent Application No. 200/0211981 disclose the use of Coriolis-based microfluidic devices for sensing the mass flow rates and densities of gases and gas mixtures, improvements in the sensitivities of such devices are necessary to fully realize the capabilities of such devices.

BRIEF DESCRIPTION OF THE INVENTION

The present invention provides a microfluidic device and sensing method that utilize a resonating tube configured to have sufficient sensitivity to be capable of sensing the volume of a gas present as bubbles in a liquid flowing through the tube, or the flow rate and/or density of a gas or gas mixture flowing through the tube.

According to a first aspect of the invention, the microfluidic device is operable to determine at least one property of a gas-containing fluid. The device includes a freestanding tube portion supported above a surface of a substrate so as to be capable of vibrating in a plane normal to the surface of the substrate. The freestanding tube portion has a continuous internal passage, a fluid inlet to the internal passage, and a fluid outlet to the internal passage, and the internal passage has a maximum internal volume of about 100 microliters. As the gas-containing fluid flows through the internal passage, a drive signal vibrates the freestanding tube portion at a resonant frequency thereof, wherein the resonant frequency is proportional to the density of the gas-containing fluid, the Coriolis effect causes the freestanding tube portion to twist about an axis of symmetry thereof while being vibrated at the resonant frequency, and the freestanding tube portion exhibits a degree of twist that varies with the mass flow rate of the gas-containing fluid. Deflections of the freestanding tube portion are sensed relative to the substrate to produce an output corresponding to the sensed deflections, and the drive signal and/or the output are assessed to determine the volume, density and/or flow rate of the gas of the gas-containing fluid.

According to a second aspect of the invention, a method is provided by which a microfluidic device is operated to determine at least one property of a gas-containing fluid. The method entails vibrating a freestanding tube portion supported above a surface of a substrate in a plane normal to the substrate surface. The gas-containing fluid is flowed through an internal passage of the freestanding tube portion, and a drive signal is generated so that the freestanding tube portion vibrates at a resonant frequency proportional to the density of the gas-containing fluid. The freestanding tube portion twists about an axis of symmetry thereof due to the Coriolis effect, and exhibits a degree of twist that varies with the mass flow rate of the gas-containing fluid. Deflections of the freestanding tube portion are sensed relative to the substrate to produce an output corresponding to the sensed deflections, and the drive signal and/or output are assessed to determine the volume, density and/or flow rate of the gas of the gas-containing fluid.

Advantages of the present invention include the ability to detect a gas phase in a microfluidic system, such air bubbles in a wide variety of liquids, as well as measure the volume of bubbles in the liquid or solution. The invention can also be used to detect, assess, and suppress or promote the nucleation of gas bubbles in various liquids. The invention also has the ability to measure the density and flow rate of an all-gas fluid, including measuring relative amounts of gases in binary gas mixtures. Finally, various tube configurations can be used to promote one or more of these aspects of the invention.

Other objects and advantages of this invention will be better appreciated from the following detailed description.

DETAILED DESCRIPTION OF THE INVENTION

Figure 1:
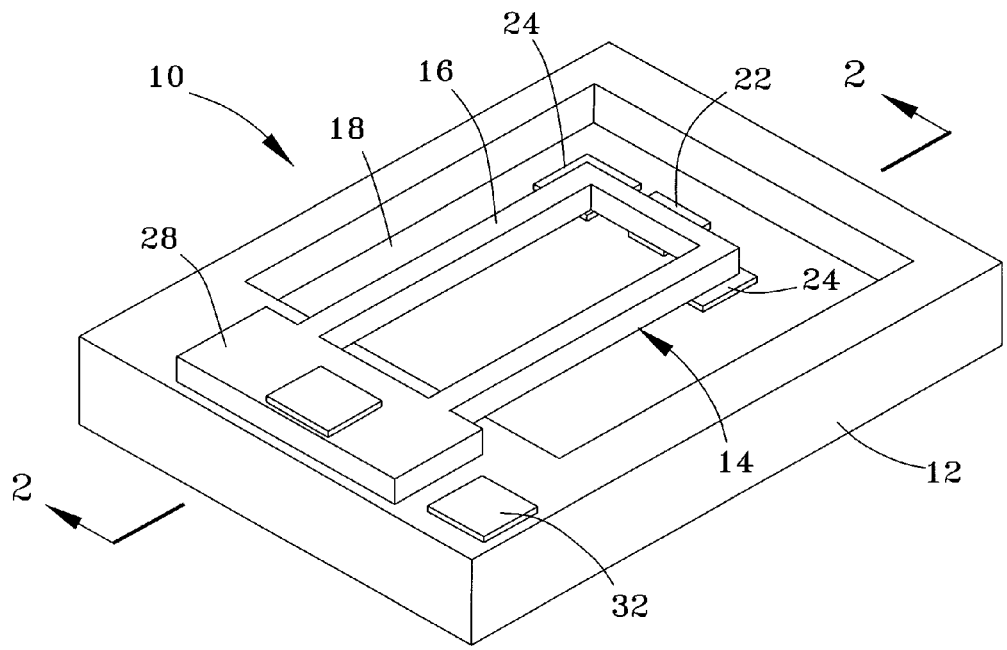
FIGS. 1 and 2 are perspective and cross-sectional views, respectively, of a microfluidic device with a resonating micromachined tube through which a fluid flows in accordance with the prior art and the present invention.

The invention provides microfluidic devices equipped with resonating micromachined tubes capable of measuring the volume of a dissolved or dispersed gas in a liquid, the flow rate and/or density of a gas or gas mixture, and the relative amounts of gases in a binary gas mixture. The invention utilizes a Coriolis-based microfluidic device of the type disclosed in Tadigadapa et al. and represented in FIGS. 1 and 2, and therefore operates on the basis that the frequency of vibration of the resonating micromachined tube 14 is proportional to the density of a liquid flowing through the tube 14, and the degree to which the freestanding portion 16 twists (deflects) during a vibration cycle as a result of the Coriolis effect can be correlated to the mass flow rate of the liquid flowing through the tube 14. Because microfluidic devices of this invention have the same operating principles and utilize components analogous to those disclosed by Tadigadapa et al., the invention will be described in reference to the device 10 of FIGS. 1 and 2, but with the understanding that the present invention presents modifications to the tube 14 for promoting its sensitivity to the extent that the volume, density and/or mass flow rate of a gas can be sensed. Exemplary tube modifications are represented in FIGS. 9 through 14, which will be discussed in greater detail below.

The ability of microfluidic devices 10 of this invention to measure properties of a gas, as opposed to measuring properties of liquids, allows the microfluidic devices 10 of this invention to have uses in a variety of additional applications and industries, including medical treatment systems such as drug infusion and anesthesia, energy and fuel systems such as fuel cells, and consumer goods such as carbonated beverages.

Figure 2:
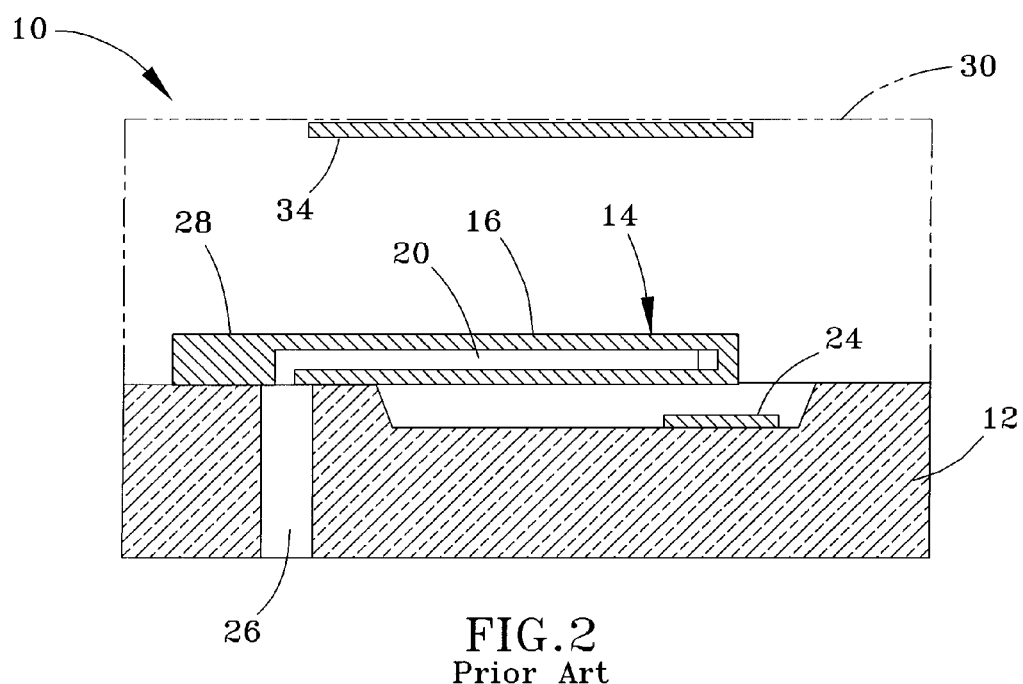

Microfluidic devices 10 of this invention can be fabricated from a variety of materials, for example, silicon (doped or undoped) or another semiconductor material, quartz, glass, ceramic, metal, polymers, and composites, using a combination of plasma and wet etching, photolithography, and wafer bonding techniques, as disclosed in Tadigadapa et al. As a nonlimiting example, such fabrication processes can be used to micromachine a silicon tube 14 and anodically bond the tube 14 to a glass substrate 12. As discussed in reference to FIGS. 1 and 2, the freestanding portion 16 of the tube 14 can be electrostatically driven into resonance and its motion capacitively sensed with the electrodes 22 and 24 and accompanying electronic circuits (not shown) connected to the device 10, such as be wire bonding. If capacitive sensing is employed, improved performance of the device 10 can be achieved by fabricating the device 10 to achieve a small gap between the tube 14 and its electrodes 22 and 24. For miniature structures, such close spacing can lead to squeeze film damping during motion, which can reduce the quality factor (Q factor or Q value) of the tube 14 and/or result in a low signal-to-noise ratio. To overcome squeeze film damping effects, the device 10 can undergo chip-level vacuum packaging. Excellent vacuum levels resulting in Q values in excess of 5000 have been obtained through chip-level vacuum packaging in combination with an integrated thin-film getter material 34, as represented in FIG. 2.

The resonating micromachined tube 14 of this invention is used to sense the density of a fluid (here, a gas, gas mixture, or gas-liquid mixture) flowing through the internal passage 20 within the freestanding portion 16 of the tube 14. The denser the fluid, the lower the resonant frequency of the tube 14. The resolution of micromachined tubes of the previously-noted commonly-assigned patents and patent applications has enabled the accurate measurement of chemical concentrations in binary liquid mixtures. However, due to its dependency on density, the resonant frequency of the tube 14 is substantially higher when a gas is flowing through the tube 14 than when a liquid is flowing through the tube 14, and the difference in resonant frequencies will depend in part on the mass and configuration of the tube 14.

The invention enables the sensing of gas volume and density with the use of very small micromachined tubes 14 whose internal volumes (as defined by their internal passages 20 within the freestanding portion 16 of the tube 14) are on the order of microliters (mL) or nanoliters (nL), and whose internal passage 20 have widths of less than 1000 micrometers. More preferably, the internal passage 20 of the freestanding portion 16 has a volume of 800 nL or less, with volumes of about 20 to about 100 nL believed to be more preferred, and a maximum width of about 100 micrometers or less, with maximum widths of about 10 to about 100 micrometers believed to be more preferred.

As taught in commonly-assigned U.S. Published Patent Application No. 2007/0157739, two-phase flow conditions such as gas bubbles in a liquid cause a fluidic damping effect that reduces the Q factor or peak gain value of a resonating tube of a Coriolis-based fluid sensing device. Large steel resonating tubes used in conventional Coriolis mass flow meters have relatively low Q values, and two-phase damping associated with gas-liquid mixtures can reduce the Q factor to broad, low-gain, low-Q values that are very difficult to track with common electronic circuitry used in industrial grade flow meters, and often result in no sensor output signal (flowmeter stalling). In contrast, micromachined tubes 14 of the present invention have very high Q values, for example, about 10,000 to about 64,000, to provide excellent frequency resolution and enable density measurements if the tube 14 is filled with a gas or a gas-liquid mixture. A circuit can be employed to lock onto and measure the frequency and gain, even if relatively lower Q peaks occur as a result of a two-phase bubble-liquid mixture.

Figure 3:
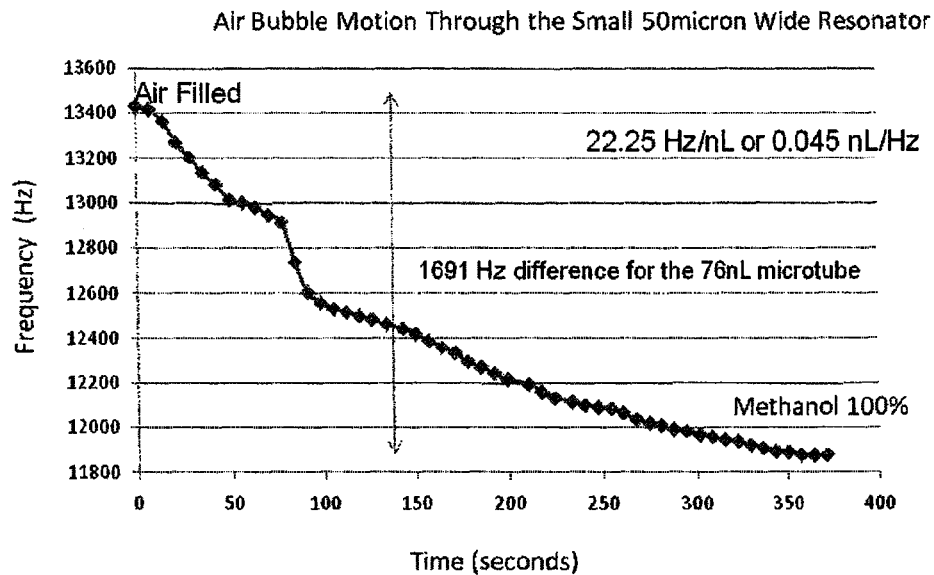
FIGS. 3 and 4 are graphs plotting the resolution capability of a microfluidic device of this invention when sensing the motion and volume of an air bubble through a resonating micromachined tube configured in accordance with an embodiment of this invention.
Figure 4:
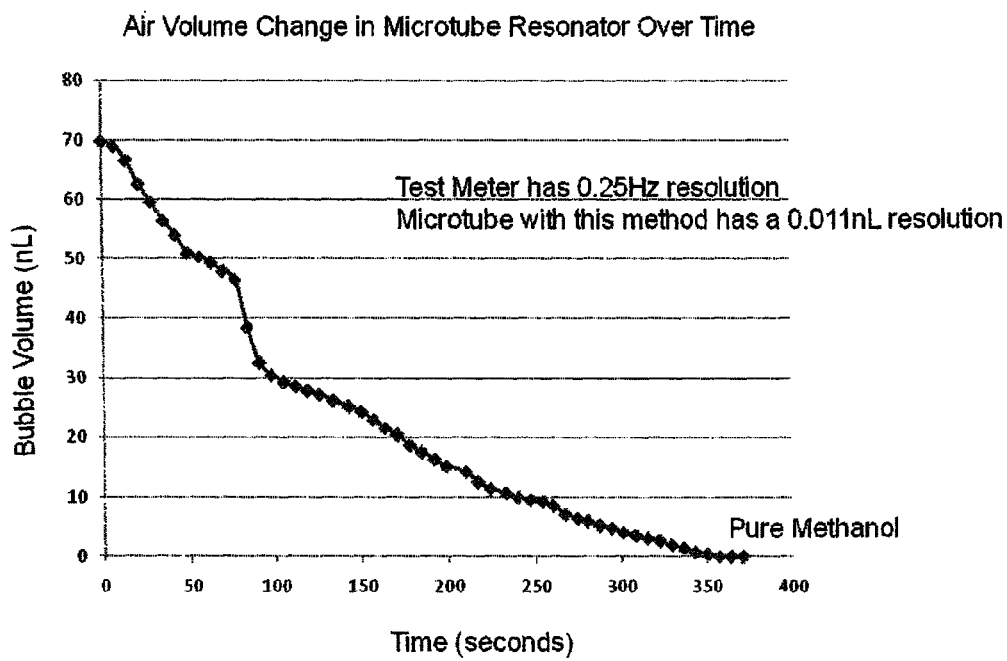

FIG. 3 is a graph plotting the resolution capability of a micromachined tube of this invention. The tube had an internal passage with an approximately square-shaped cross-section having a width of about fifty micrometers, and the volume of the internal passage within the freestanding portion of the tube was about 76 nL. The device employed a control loop that adjusted the drive signal to the tube to control the vibration of the tube and maintain a frequency at or near its resonant frequency. The plot represents the passage of an approximately 70 nL air bubble (density of about 0.0012 g/cc at 25° C.) through methanol (density of about 0.79 g/cc at 20° C.) flowing through the tube over a span of about six minutes. The frequency resolution seen in FIG. 3 was about 45 picoliters per Hertz, which was sufficient to resolve the volume of air within the methanol as shown by the graph of FIG. 4. From FIGS. 3 and 4, it was concluded that changes in resonant frequency attributed to changes in the density of a gas-liquid mixture can be employed to not only detect a gas bubble in a liquid, but also the volume of gas in the liquid.

Figure 5:
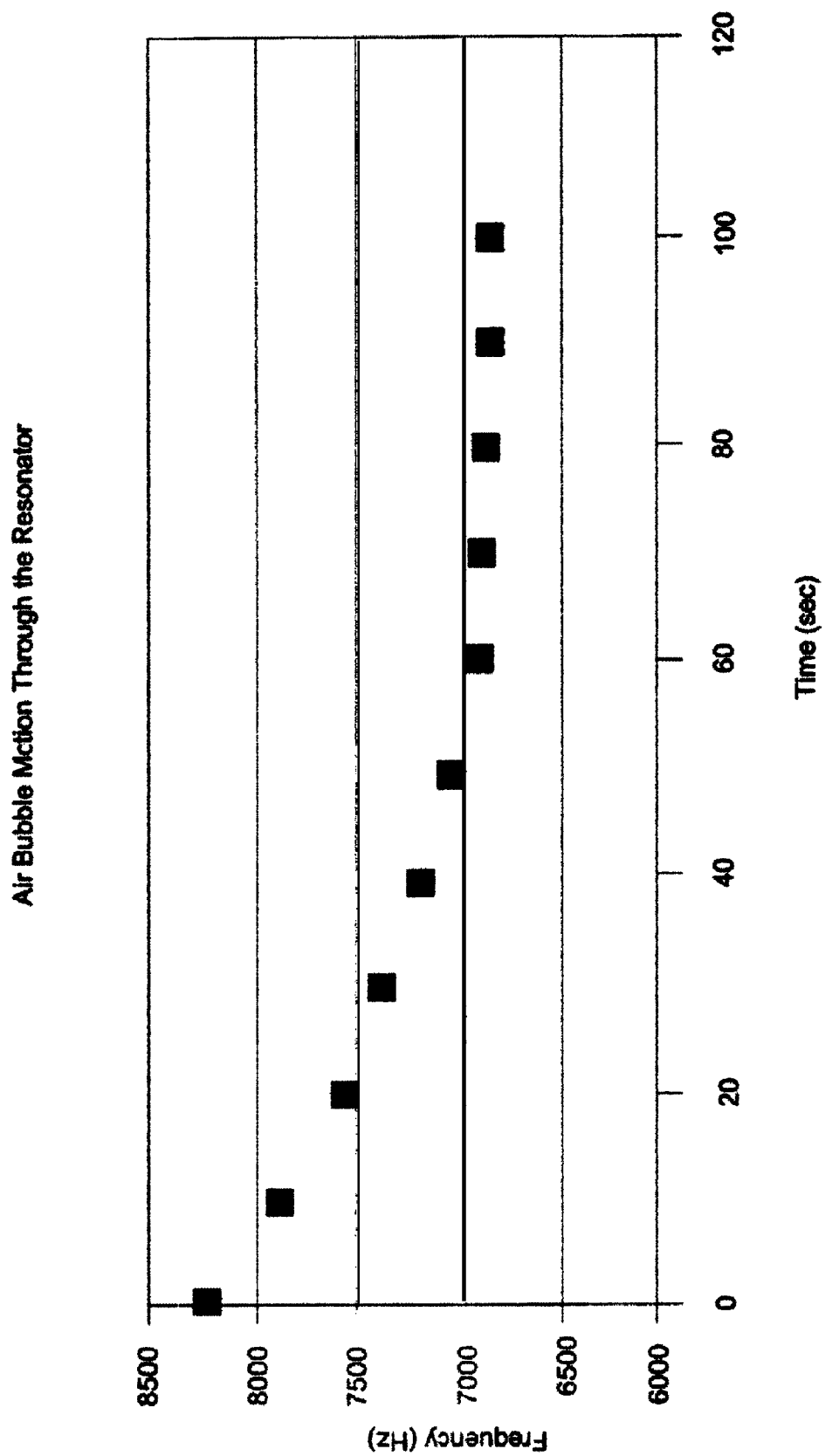
FIG. 5 is a graph plotting the resolution capability of a microfluidic device of this invention when sensing the motion of an air bubble through a resonating micromachined tube configured in accordance with an embodiment of this invention.

FIG. 5 is another graph plotting the resolution capability of a micromachined tube of this invention when evaluating a two-phase gas-liquid mixture. As before, the device employed a control loop to maintain the vibration of the tube at or near its resonant frequency. The plot represents the passage of air (density of about 0.0012 g/cc at 25° C.) in diesel fuel (density of about 0.81 g/cc at 20° C.) flowing through the tube over a span of about two minutes. At time zero, the tube was entirely filled with air and its resonant frequency was about 9055 Hz. The resonant frequency of the tube dropped as the volume fraction of the air bubble (slug) within the passage decreased, until the tube was completely purged of the air bubble and the resonant frequency of the liquid-filled tube was about 6840 Hz. As the volume of air in the tube decreased, the peak gain value of the tube also increased. At a frequency of about 8227 Hz, the peak signal gain value was only about −53 dB with a Q value under 100, evidencing a large fraction of the tube being filled with air. At a frequency of about 7215 Hz, the peak gain value was about −40 dB. Once the air bubble was purged from the tube, the gain value returned to about −13 dB. The transient two-phase (gas-liquid) condition had a much larger impact on lowering the Q and peak gain values than the single-phase (liquid only) condition, evidencing the capability of using the Q value of the tube to determine the gas volume in a gas-liquid mixture.

Figure 6:
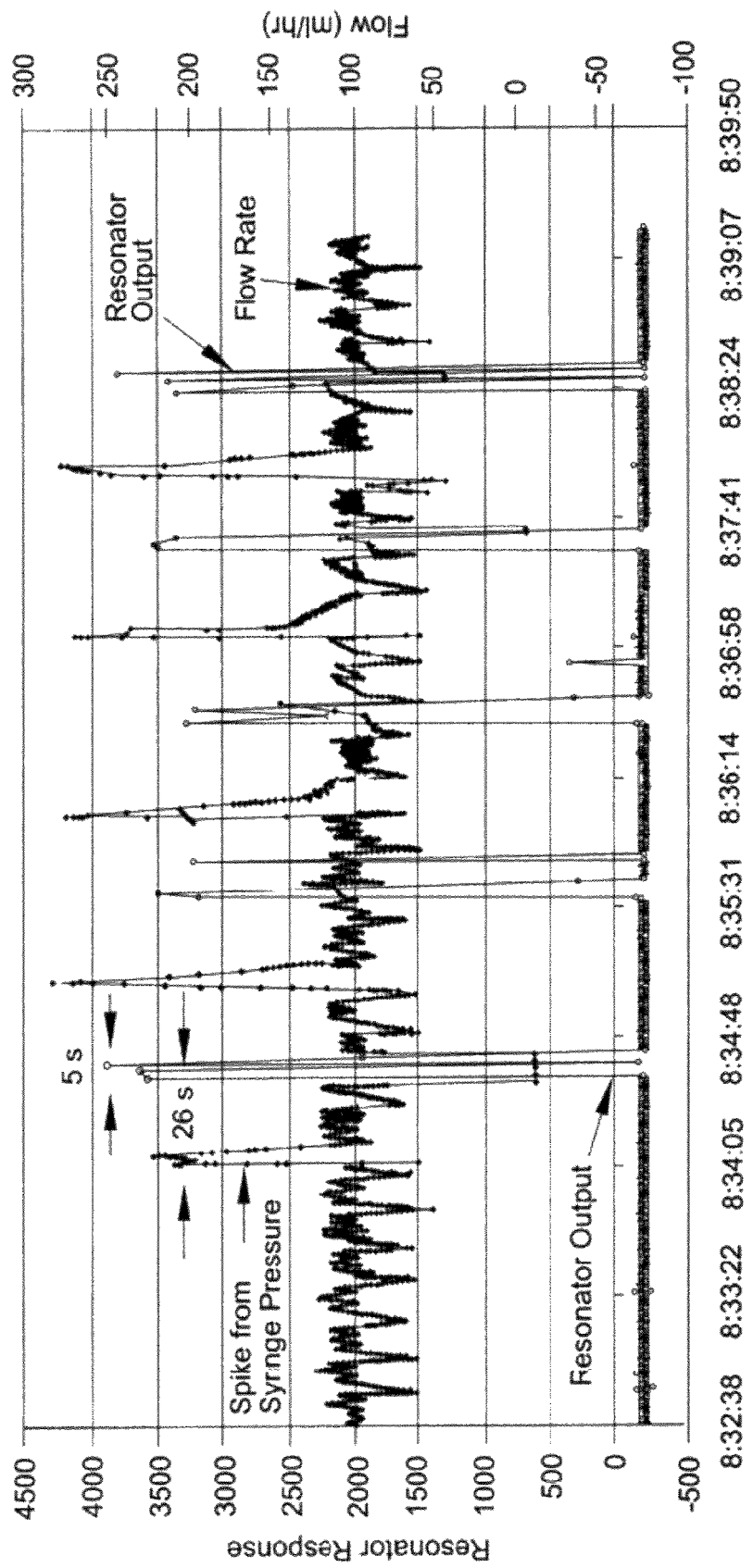
FIG. 6 is a graph plotting the response of a microfluidic device of this invention when air bubbles are injected into water flowing through a resonating micromachined tube configured in accordance with an embodiment of this invention.

FIG. 6 is a graph plotting the effect of sequentially injecting five approximately 50 microliter air bubbles into water flowing through an IV tubing set of a peristaltic drug pump upstream of a microfluidic device of this invention. The device employed a gain control loop that automatically adjusted the drive signal to the tube to maintain a fixed amplitude. As seen in FIG. 6, each injection caused a brief pressure spike resulting in a flow rate spike. About twenty-six seconds after the first injection, the output of the device rose sharply, indicating that the gain control loop had increased the drive signal to compensate for damping of the resonating tube caused by the air bubble. The first air bubble took approximately five seconds to pass through the resonating tube, as evidenced by the duration of the increased drive output seen in FIG. 6. As such, FIG. 6 evidenced that an air bubble can be detected in a liquid stream (for example, an IV solution) based on the drive signal response from a gain control loop operating to maintain a resonating tube at a fixed amplitude. It is possible to correlate the volume of a gas bubble based on the drive output.

Figure 7:
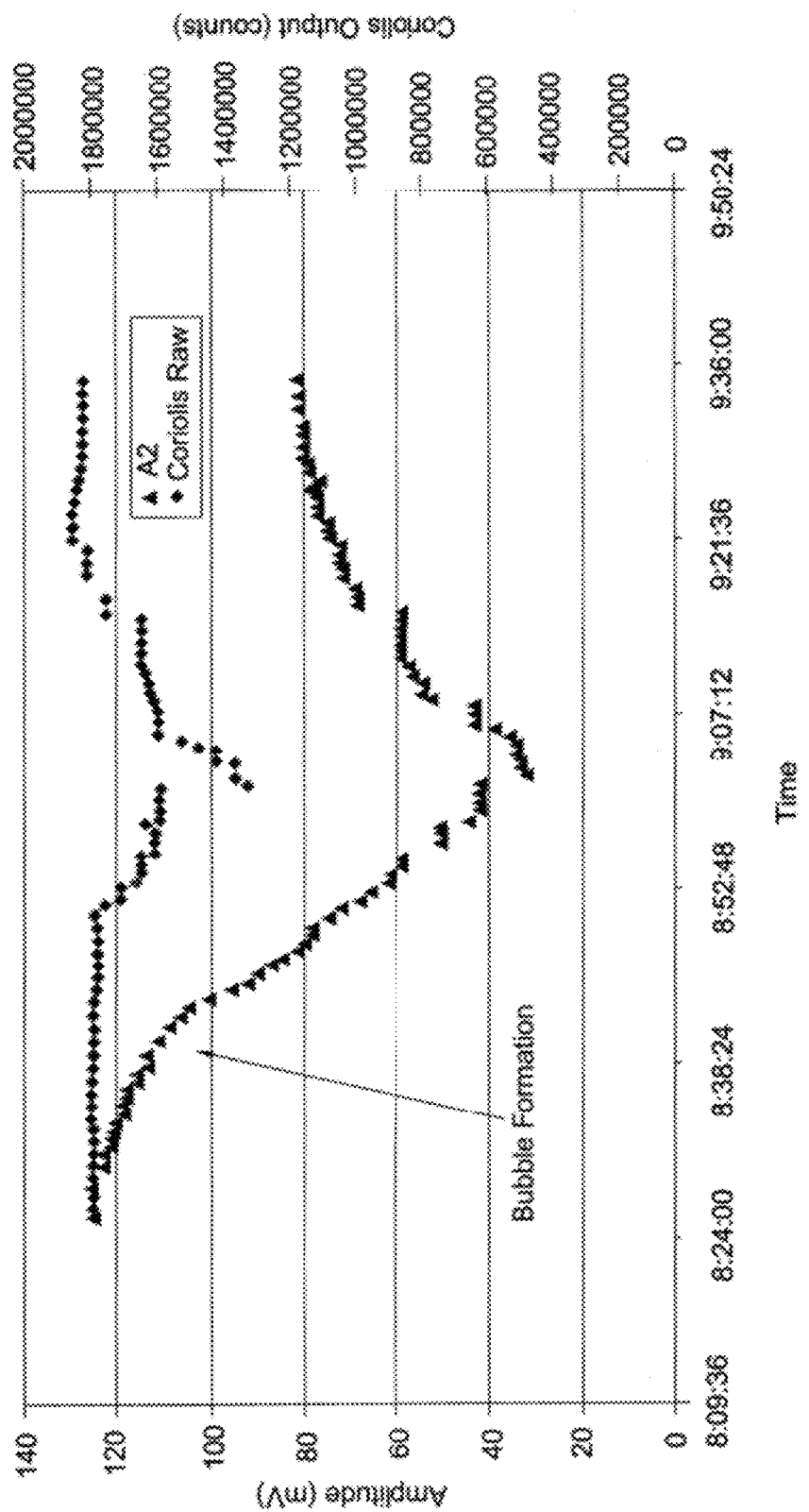
FIG. 7 is a graph plotting a decrease in resonator amplitude and sensor output due to gas bubble nucleation and growth within a resonating micromachined tube configured in accordance with an embodiment of this invention.

Nucleation and growth of air bubbles have been documented in certain microtube designs and drive conditions. FIG. 7 depicts what has been hypothesized to be evidence of the growth of an air bubble in a micromachined tube through which de-ionized water was flowing. The de-ionized water, termed "gassy" because it had not been degassed via boiling, was delivered to the tube at a rate of about 100 mg/hr. In contrast to the control operating mode of the microfluidic device used to produce the graph of FIG. 6, the resonating tube was driven at a constant voltage level, with the result that a decrease in the tube amplitude would indicate a change in the damping of the vibrating tube. The twist or Coriolis output of the tube (used to measure mass flow rate) would be similarly affected by damping. As evident from FIG. 7, without an amplitude control loop, the bubble significantly reduced the amplitude, leading to an error in the measurement of the constant flow rate of water through the tube (the amplitude was restored FIG. 7 by injecting a high flowrate pulse of water with a syringe). In many cases, even with an amplitude control loop, conventional control circuits might not be able to fully compensate for the damping effect indicated in FIG. 7, resulting in mass flow rate output errors.

Figure 8:
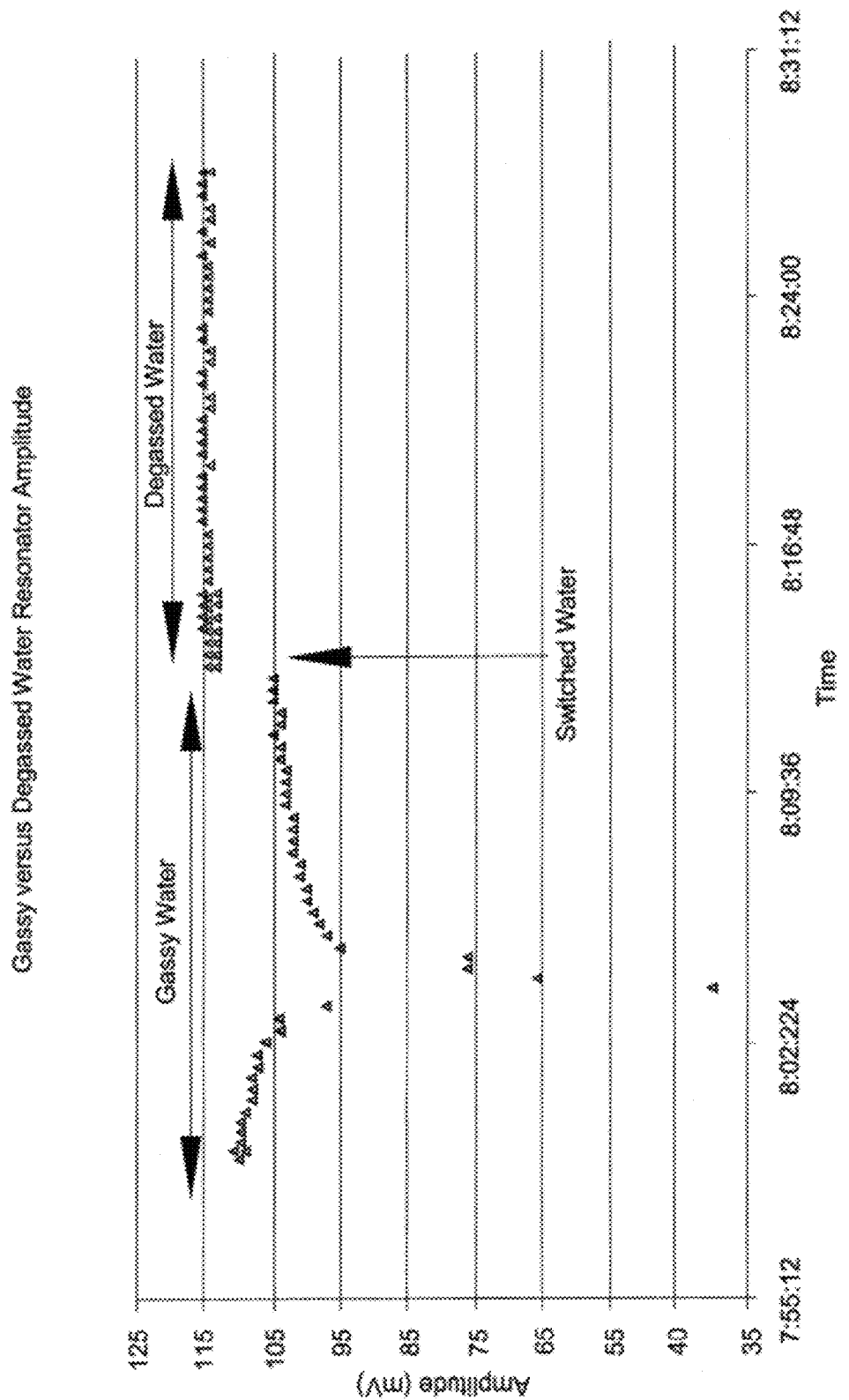
FIG. 8 is a graph evidencing an amplitude reduction observed with a gassy water sample in comparison to a degassed water sample when passed through a resonating micromachined tube configured in accordance with an embodiment of this invention.

FIG. 8 represents data obtained from a similar evaluation performed with gassy de-ionized water and degassed de-ionized water and using the same microfluidic device. The amplitude reduction observed with the gassy water sample of FIG. 7 is evident on the lefthand side of the graph of FIG. 8 corresponding to the gassy sample, but is absent from the righthand side of FIG. 8 corresponding to the degassed sample, evidencing that air bubble nucleation and growth did not occur in the degassed water sample. During additional evaluations, it was observed that similar amplitude reductions did not occur with gassy water samples that were not flowing (stagnant) or were flowing at high flow rates, suggesting a correlation to flow rate and bubble nucleation. The observations represented in FIGS. 7 and 8 suggest that air bubbles are able to nucleate on the inner walls of a small micromachined tube, and that the bubbles can grow to a size sufficient to damp the amplitude of tube vibration. This conclusion is supported by the fact that bubbles are nucleated under ultrasonic conditions, as in the case of ultrasonic cleaning techniques. For example, ultrasonic frequencies in a range of about 25 kHz to more than 1 MHz are often employed to nucleate bubbles and cause cavitation and bubble streaming to enhance cleaning of such products as silicon wafers. Resonant frequencies of the micromachined tubes used in the above investigations were in a range of about 10 KHz to about 35 KHz, and therefore overlap frequencies intentionally used to ultrasonically nucleate bubbles. Developing an understanding of bubble nucleation and growth in two-phase mixtures has the potential for broadening the scope of applications for Coriolis microfluidic devices of this invention, as well as offer ways in which bubble nucleation can be suppressed to improve the accuracy and reliability of the microfluidic device 10 of this invention, as well as other devices such as industrial densitometers, fuel cell concentration sensors, Coriolis mass flow meters, and drug pumps and monitors. It is also possible to intentionally promote the bubble nucleation phenomenon in technologies such a cell lysis and measurement of the rheological property of fluids.

The tendency for bubble nucleation and growth may also be influenced by the tube material. For example, nucleation may by promoted or inhibited by forming the tube or coating the internal passage of the tube with a hydrophilic or hydrophobic material, such as silicon and silicon dioxide (silica). Various tube configurations may also play a role in promoting and inhibiting bubble nucleation, for example, by altering the cross-sectional shape or increasing or decreasing the cross-sectional area of the internal passage within a tube, or increasing or decreasing the radii of corners of the tube.

The gas volume sensitivities evidenced by FIGS. 3 through 8 suggest the use of microfluidic devices of this invention in various applications in which gas-liquid mixtures are used, including pharmaceutical processing, cell handling, DNA and genetic testing, pill coating and capsule filling. By coupling a micromachined tube 14 of this invention to a small valve and pump, control is possible of fluid volumes at the nanoliter and picoliter level. For example, the microfluidic device of this invention is capable of improving gas bubble detection and measurement in medication delivery systems and overcome problems experienced with two-phase damping in resonant sensing systems. Air bubbles in drug infusion and intravenous lines can lead to air embolisms and death. By locating a microfluidic device of this invention as part of a flow meter and monitoring system of a drug infusion or intravenous line, the drug or IV solution can be flowed through the device 10 and its resonating tube 14 to detect bubbles prior to entering the patient.

The small volume measurement capability of the microfluidic device also enables the detection and measurement of carbon dioxide ($CO_2$) contents and bubble contents in methanol-water solutions used in fuel cells, for example, direct methanol fuel cell (DMFC) systems that generate carbon dioxide bubbles during the electricity generating process. These bubbles can affect the performance of the fuel cell if not vented, and a microfluidic device 10 equipped with a micromachined tube 14 of this invention can be used to monitor and assist in controlling dissolved and nucleated gases in a fuel cell fuel stream. Additional resonating tubes can be employed to measure the methanol to water ratio in accordance with U.S. Published Patent Application No. 2007/0157739.

The ability to sense and measure gas volumes in a liquid can also be used to monitor processes in which a gas is bubbled through a liquid, in which the liquid is picked up by the gas and makes up an appreciable percent of the total output gas.

The sensitivity of the microfluidic device also enables the monitoring of microbubble nucleation of two-phase solutions during ultrasonic vibration of the resonating micromachined tube 14. For example, applications for dissolved gases exist in the carbonated beverage market and energy applications where hydrogen, natural gas or other flammable gases may be stored in a liquid, often a liquid fuel. The amount of dissolved gas in a liquid can be determined based on a baseline density of the liquid and the density measured for the gassy liquid. For example, two devices can be differentially employed to compare the densities of a liquid with and without dissolved gas. Alternatively, the same device can be used to evaluate gassy and degassed samples of the same liquid.

In addition to monitoring and measuring gas content in a gas-liquid mixture based on resonant frequency, the above investigations further evidenced that dissolved gas levels can be measured by examining the Q and peak gain values. It is believed that particular applications in which this technique could be used include detecting the presence of helium in isopropyl alcohol, $CO_2$ levels in water or beverages to measure carbonation, and oxygen and $CO_2$ levels in blood and other bodily fluids.

The sensitivity of the resonating micromachined tubes 14 of this invention further permit the measurement of the density and flow rate of a gas or gas mixture and the relative amounts of gases in a binary gas mixture. Micromachined tubes 14 within the scope of this invention have been successfully employed to distinguish nitrogen, helium, hydrogen, argon, carbon dioxide, nitrous oxide, and oxygen from each other on the basis of density. This capability enables the measurement of the amounts of oxygen (1.33 mg/cc) and nitrous oxide (1.84 mg/cc) in dental anesthesia to insure the patient is getting sufficient oxygen and avoid a nitrous oxide overdose. Other fields in which control of the content of a binary gas mixture include, but are not limited to, the semiconductor field, for example, forming gas mixtures of $H_2$ and $N_2$. Calibration of the microfluidic device for sensing a binary gas mixture can entail separately sampling each gas with the device to determine its density, thereby identifying two data points from which the relative concentrations of the gases can be determined in mixtures of the gases.

In addition to limiting the cross-sectional flow area and volume within the freestanding portion 16 of the tube 14 as discussed above, modified tube configurations of the types represented in FIGS. 9 through 14 are believed to be particularly effective in promoting the ability of the micromachined tube 14 to sense the mass flow rate and density of a gas or gas mixture. Generally, the tube configurations represented in FIGS. 9 through 14 utilize stiffening bars, tube shapes, rounded corners, and wall thickness to improve the performance of the tubes 14 for gas flow applications.

Figure 9:
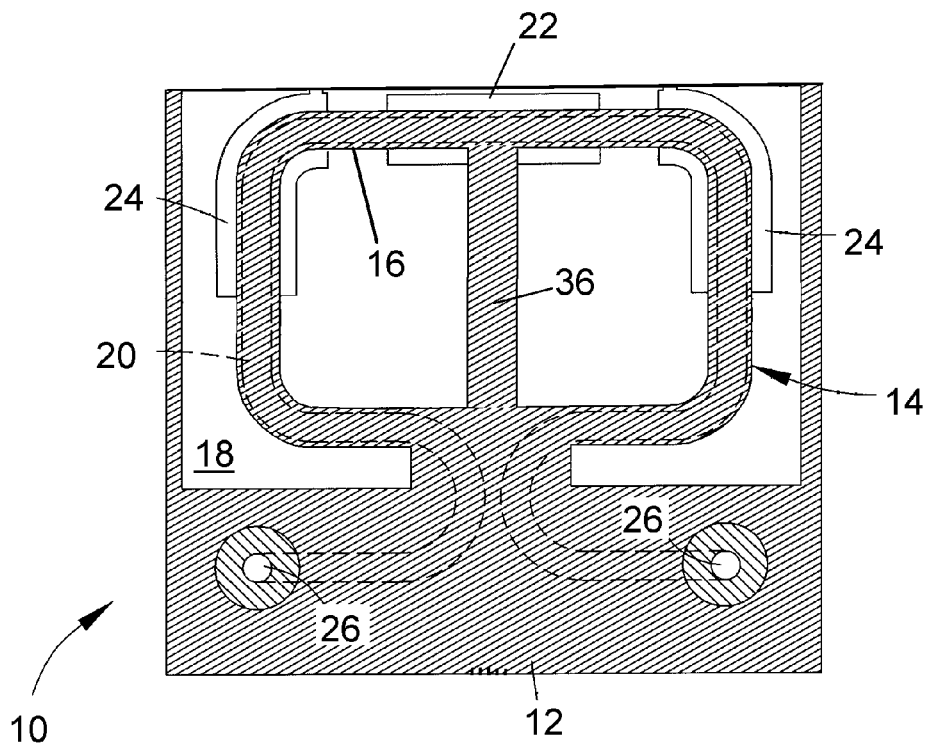
FIGS. 9 through 14 are plan views schematically representing micromachined tubes capable of exhibiting heightened sensitivity to gases in accordance with preferred embodiments of this invention.
Figure 10:
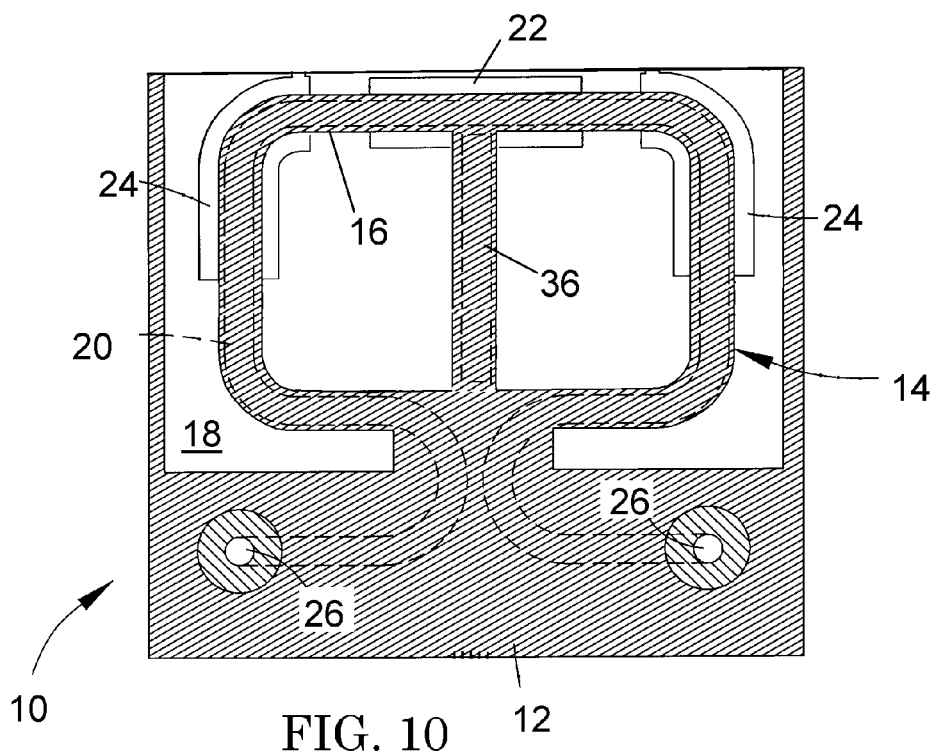
Figure 11:
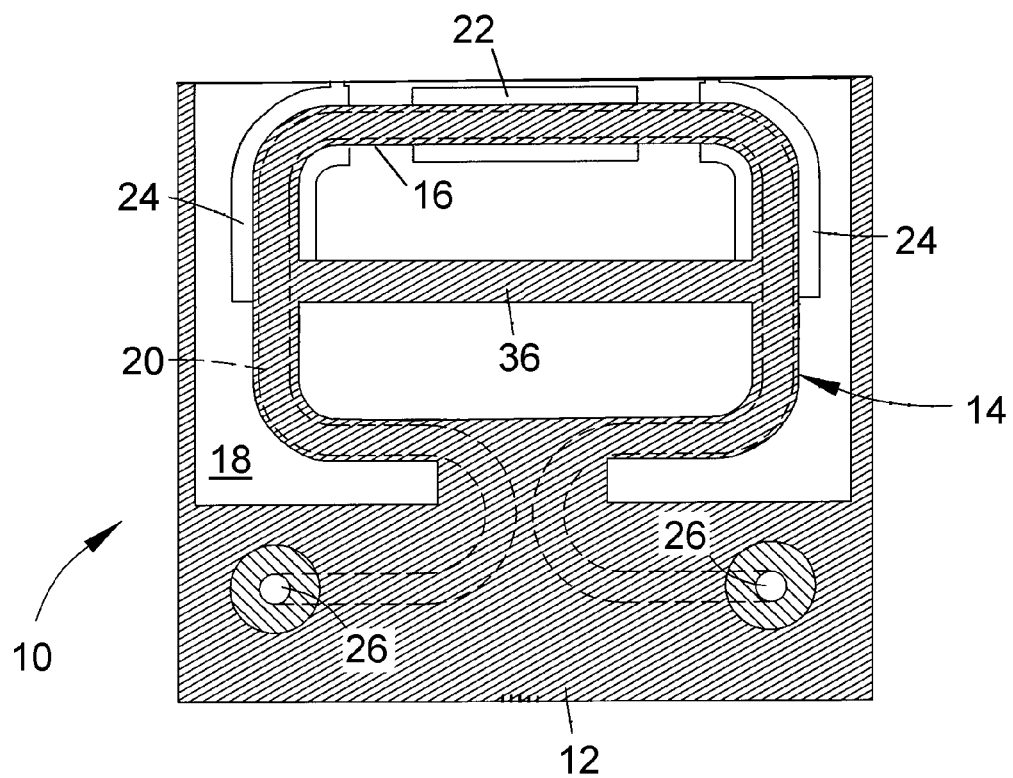
Figure 12:
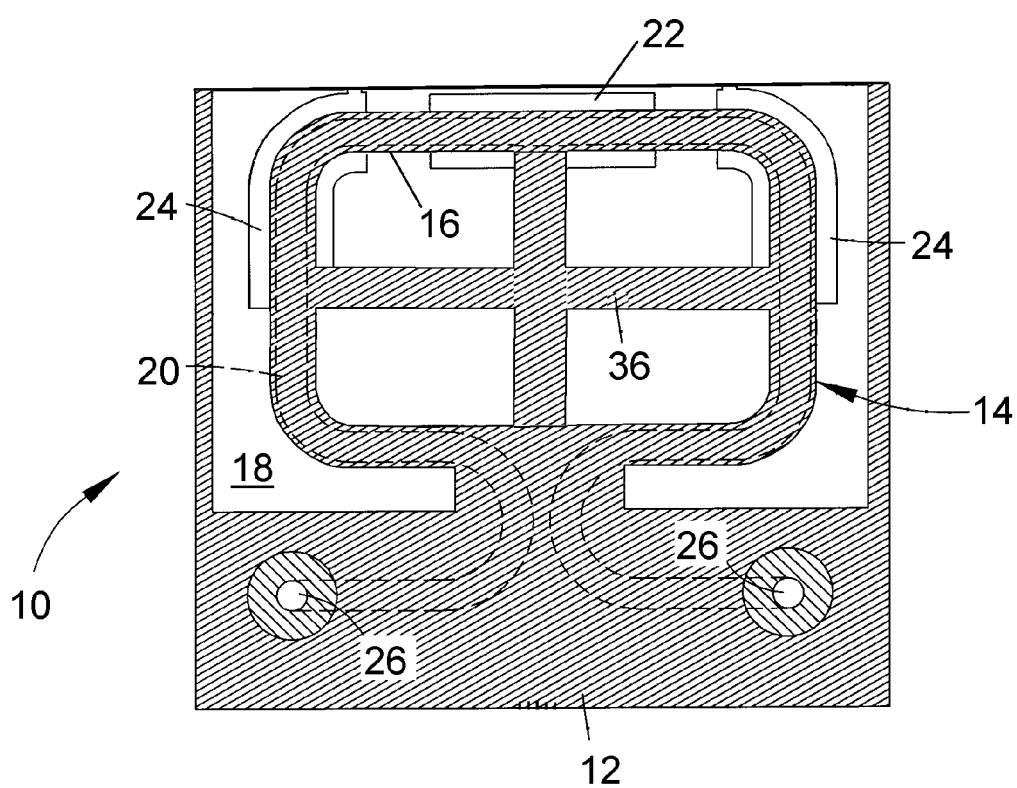

High gas flow rates can cause a resonating micromachined tube to vibrate in alternative modes at frequencies different that would occur if a liquid was being evaluated. This phenomenon is believed to be due to much lower internal fluidic damping of the tube with gases as compared to liquids. To avoid alternative vibration modes, the tubes 14 represented in FIGS. 9 through 12 incorporate one or more crossbars to stiffen the tube 14 and thereby reduce the likelihood of an alternate resonate mode developing during gas flow through the tube 14. The tube configurations in FIGS. 9 through 12 are defined herein as having C-shaped freestanding portions 16, as opposed to the U-shaped freestanding portion 16 of FIG. 1. In FIG. 9, the tube 14 is equipped with a solid crossbar 36 on its axis of symmetry about which the tube 14 twists due to the Coriolis effect. The tube 14 of FIG. 10 has a similarly aligned but hollow crossbar 36 to improve the density resolution by minimizing the mass of the tube 14. The crossbar 36 of FIG. 11 is oriented transverse to the twist axis, roughly equally dividing the opening surrounded by the tube 14, to suppress undesirable vibrational modes. The rigidity of the tube 14 shown in FIG. 12 is further promoted by combining the crossbar forms of FIGS. 9 and 11.

Figure 13:
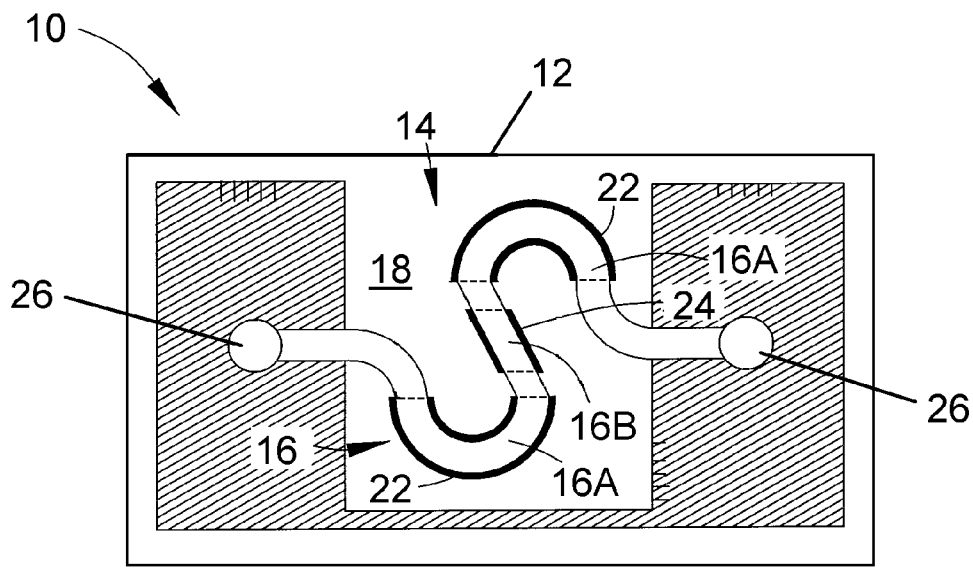

The freestanding portion 16 of the tube 14 depicted in FIG. 13 is not cantilevered (as are the previous configurations), but instead is configured as an S-shaped tube. The drive electrodes 22 are placed under curved segments 16A of the freestanding portion 16, and a sensing electrode 24 is located beneath the generally straight intermediate segment 16B between the curved segments 16A. The drive electrodes 22 are operated to cause the freestanding portion 16 to twist, causing the intermediate segment 16B to periodically deflect toward and away from the substrate surface 18 beneath the freestanding portion 16.

Figure 14:
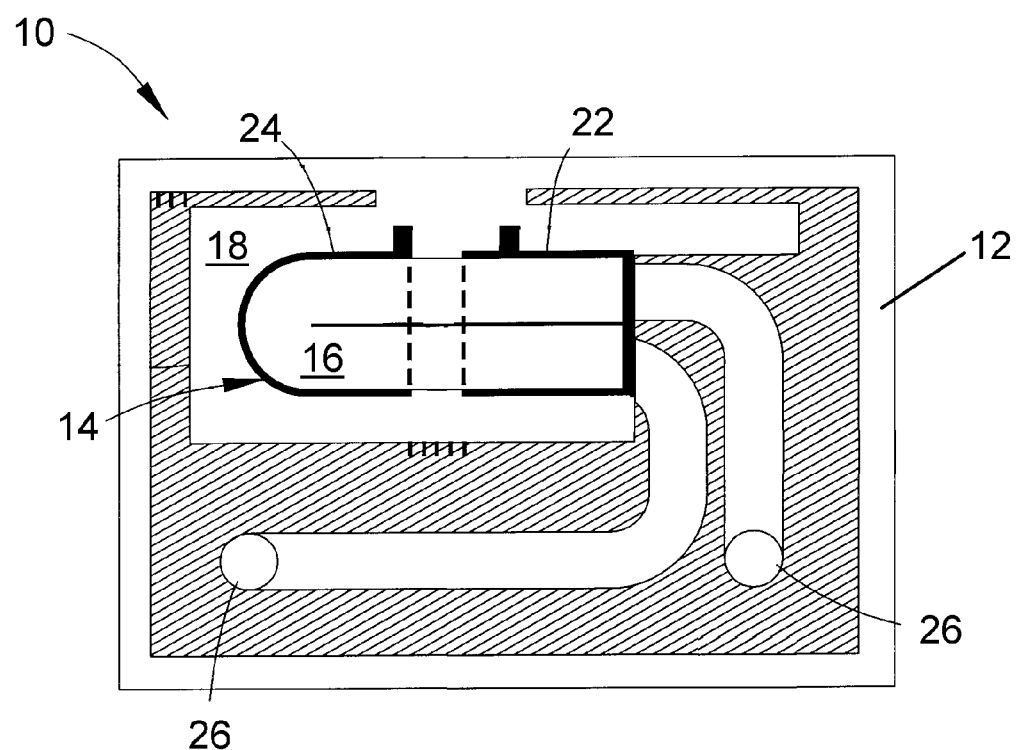

Finally, the tube 14 depicted in FIG. 14 has a compact freestanding portion 16 whose cantilevered length is about three times or more greater than its transverse width. The compact configuration for the freestanding portion 16 minimizes the amount of material required for the tube 14 and thereby increases the density sensitivity of the tube 14. The compact cantilevered tube 14 of FIG. 14 is particularly well suited for sensing the density and mass flow rate of a gas or gas mixture. The sensitivity of the tube 14 is sufficient to monitor the flow rate and relative amounts of two gases in a gas mixture, for example, nitrous oxide and oxygen in anesthesia, enabling the mixing of nitrous oxide and oxygen to be controlled.

To permit higher gas flow rates without causing vibrational instability, external damping can also be employed. For example, the pressure that surrounds the resonating tubes 14 of FIGS. 1, 2 and 9 through 14 could be increased by reducing the amount of getter material 34 within the enclosure or changing the material of the getter material 34. Alternatively, the getter material 34 could be eliminated, as could the capping wafer 30 and/or the vacuum packaging to permit squeeze film damping of the tube 14. Lateral piezoelectric or magnetic drives could also be employed to increase external damping of the tube 14. Improved high pressure performance can also be promoted by increasing the thickness of the tube wall and increasing the radii of the corners of the tubes 14 to reduce the pressure drop through the tube 14.

Because high internal gas pressures within the tube 14 can introduce an error in the density output of the resonating tube 14 by increasing the stiffness of the tube 14, affecting the resonant frequency of the tube 14, an absolute pressure sensor may be useful to provide feedback for improving the accuracy of the device 10. A pressure sensor (not shown) of any suitable type can be provided as a discrete manometer added in series to the device 10, or incorporated on the same substrate 12 as the tube 14. Because temperature can also introduce errors in density measurements, a temperature sensor (not shown) can be incorporated into the device 10 or otherwise provide feedback to factor the temperature of the fluid being assessed when calculating density.

Various other components can be combined with the device 10 to add a desirable functionality, such as controllers and valves to help regulate or stop flow through the tube 14 or a fluid system being monitored by the device 10. For example, the gas concentration output of the device 10 can be used to control a valve capable of stopping the flow of a gas mixture being monitored by the device if a dangerous combination of gases is detected, for example, an improper anesthesia mixture of nitrous oxide and oxygen.

While the invention has been described in terms of certain embodiments, it is apparent that other forms could be adopted by one skilled in the art. Therefore, the scope of the invention is to be limited only by the following claims.

The invention claimed is:

1. A method of determining at least one property of a gas-containing fluid comprising at least a first gas in at least a first fluid, the method comprising:
   providing a freestanding tube portion supported above a surface of a substrate so as to be capable of vibrating in a plane normal to the surface of the substrate, the freestanding tube portion having a continuous internal passage, a fluid inlet portion of the internal passage through which the gas-containing fluid enters the freestanding tube portion, and a fluid outlet portion of the internal passage through which the gas-containing fluid exits the freestanding tube portion;
   flowing the gas-containing fluid through the internal passage of the freestanding tube portion;
   generating a drive signal to vibrate the freestanding tube portion at a resonant frequency thereof and avoid alternative vibration modes of the freestanding tube portion, wherein the resonant frequency is proportional to the density of the gas-containing fluid, the Coriolis effect causes the freestanding tube portion to twist about an axis of symmetry thereof while being vibrated at the resonant frequency, and the freestanding tube portion exhibits a degree of twist that varies with the mass flow rate of the gas-containing fluid;
   sensing deflections of the freestanding tube portion relative to the substrate and producing an output corresponding to the sensed deflections; and
   assessing the drive signal and the output to determine at least the volume of the first gas in the gas-containing fluid.

2. The method according to claim 1, wherein the first fluid is a liquid.

3. The method according to claim 2, wherein the gas-containing fluid consists of the first gas in the liquid.

4. The method according to claim 2, wherein the assessing step comprises correlating the resonant frequency of the freestanding tube portion to the volume of the first gas in the liquid.

5. The method according to claim 2, wherein the drive signal is controlled to maintain a substantially constant vibration amplitude of the freestanding tube portion, and the assessing step comprises correlating the drive signal of the generating means to the volume of the first gas in the liquid.

6. The method according to claim 2, wherein the first gas is dissolved in the liquid.

7. The method according to claim 6, wherein the assessing step comprises detecting bubbles of the first gas in the liquid within the freestanding tube portion.

8. The method according to claim 7, wherein the vibration of the freestanding tube portion nucleates bubbles of the first gas in the liquid.

9. The method according to claim 6, wherein the device is installed in a fuel cell system, the gas-containing fluid is a fuel cell solution, and the assessing step comprises detecting bubbles of the first gas in the fuel cell solution within the freestanding tube portion.

10. The method according to claim 1, wherein the first fluid is a second gas.

11. The method according to claim 10, wherein the assessing step further comprises correlating the resonant frequency of the freestanding tube portion to the density of the gas-containing fluid.

12. The method according to claim 10, wherein the assessing step comprises correlating the resonant frequency of the freestanding tube portion to the relative amounts of the first and second gases in the gas-containing fluid.

13. The method according to claim 1, further comprising applying external damping to the freestanding tube portion.

14. The method according to claim 1, wherein the internal passage has a maximum internal volume of about 100 micro liters.

15. A method of determining at least one property of a gas-containing fluid comprising at least a first gas dissolved in a liquid, the method comprising:
providing a freestanding tube portion supported above a surface of a substrate so as to be capable of vibrating in a plane normal to the surface of the substrate, the freestanding tube portion having a continuous internal passage, a fluid inlet portion of the internal passage through which the gas-containing fluid enters the freestanding tube portion, and a fluid outlet portion of the internal passage through which the gas-containing fluid exits the freestanding tube portion;
flowing the gas-containing fluid through the internal passage of the freestanding tube portion;
generating a drive signal to vibrate the freestanding tube portion at a resonant frequency thereof and avoid alternative vibration modes of the freestanding tube portion, wherein the resonant frequency is proportional to the density of the gas-containing fluid, the Coriolis effect causes the freestanding tube portion to twist about an axis of symmetry thereof while being vibrated at the resonant frequency, and the freestanding tube portion exhibits a degree of twist that varies with the mass flow rate of the gas-containing fluid;
sensing deflections of the freestanding tube portion relative to the substrate and producing an output corresponding to the sensed deflections; and
assessing the drive signal and the output to determine at least the volume of the first gas in the gas-containing fluid.

16. The method according to claim 15, wherein the assessing step comprises detecting bubbles of the first gas in the liquid within the freestanding tube portion.

17. The method according to claim 16, wherein the vibration of the freestanding tube portion nucleates bubbles of the first gas in the liquid.

18. The method according to claim 15, wherein the device is installed in a fuel cell system, the gas-containing fluid is a fuel cell solution, and the assessing step comprises detecting bubbles of the first gas in the fuel cell solution within the freestanding tube portion.

19. The method according to claim 15, further comprising applying external damping to the freestanding tube portion.

20. The method according to claim 15, wherein the internal passage has a maximum internal volume of about 100 micro liters.

* * * * *